US005843905A

United States Patent [19]

Singh et al.

[11] Patent Number: 5,843,905

[45] Date of Patent: Dec. 1, 1998

[54] PEPTIDIC PHOSPHINYLOXYMETHYL KETONES AS INTERLEUKIN-1β-CONVERTING ENZYME INHIBITORS

[75] Inventors: Jasbir Singh, Gilbertsville; Roland E. Dolle, King of Prussia; Gary Speier, Phoenixville, all of Pa.

[73] Assignee: Vertex Pharmaceuticals, Incorporated, Cambridge, Mass.

[21] Appl. No.: 597,346

[22] Filed: Feb. 6, 1996

Related U.S. Application Data

[63] Continuation of Ser. No. 248,791, May 25, 1994, abandoned, which is a continuation-in-part of Ser. No. 73,219, Jun. 4, 1993, abandoned.

[51] Int. Cl.$^{6}$ .......................... A61K 38/06; A61K 38/00; C07K 5/00; C07K 7/00

[52] U.S. Cl. .............................. 514/18; 514/19; 530/331; 544/182

[58] Field of Search ........................ 514/18, 19; 530/331; 544/182

[56] References Cited

U.S. PATENT DOCUMENTS

| | | | |
|---|---|---|---|
| 5,055,451 | 10/1991 | Krantz et al. . | |
| 5,462,939 | 10/1995 | Dolle et al. | 514/231.5 |
| 5,585,486 | 12/1996 | Dolle et al. | 544/182 |

FOREIGN PATENT DOCUMENTS

| | | | |
|---|---|---|---|
| 0 519748 A2 | 6/1992 | European Pat. Off. . | |
| WO 91/15577 | 10/1991 | WIPO . | |
| WO 93/05071 | 3/1993 | WIPO | C07K 13/00 |
| WO 93/09135 | 3/1993 | WIPO | C07K 5/04 |

*Primary Examiner*—Douglas W. Robinson
*Assistant Examiner*—S. G. Marshall
*Attorney, Agent, or Firm*—Fish & Neave; James F. Haley, Jr.; Lisa A. Dixon

[57] ABSTRACT

Disclosed are compounds, compositions and methods for inhibiting interleukin -1β protease activity, the compounds having the structure of formula (1) as described in the specification.

8 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: -1
( D ) OTHER INFORMATION: /label=TRITC
/ note= "TRITC is tetramethylrhodamine isothiocyanate".

( i x ) FEATURE:
( A ) NAME/KEY: Modified-site
( B ) LOCATION: 11
( D ) OTHER INFORMATION: /label=Xaa
/ note= "Xaa is NH2".

( x i ) SEQUENCE DESCRIPTION: SEQ ID NO: 1:

Ala Tyr Val His Asp Ala Pro Val Arg Ser
1 5 10

PEPTIDIC PHOSPHINYLOXYMETHYL KETONES AS INTERLEUKIN-1β-CONVERTING ENZYME INHIBITORS

CROSS-REFERENCE TO RELATED APPLICATIONS

This application is a continuation of application Ser. No. 08/248,791, filed May 25, 1994, now abandoned, which is a continuation-in-part of Ser. No. 08/73,219, filed Jun. 4, 1993 now abandoned.

BACKGROUND OF THE INVENTION

1. Field of the Invention

This invention relates to a series of novel amino acid, di- and polypeptide analogs which exhibit selective inhibition of interleukin-1β-converting enzyme, to compositions containing the novel amino acid analogs and methods for therapeutic utility. The interleukin-1β-converting enzyme inhibitors described in this invention comprise novel aspartic acid-derived phosphinyloxymethyl ketones which possess particular utility in the treatment of inflammatory and immune-based diseases and cancer.

2. Reported Developments

Interleukin 1β (IL-1β) protease (also known as interleukin 1β converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A., *Proc. Nat. Acad. Sci.,* (1989), 86, 5227–5231 and Black, R. A.; Kronheim, S. R.; Sleath, P. R., *FEBS Let.,* (1989), 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, acute and chronic myelogenous leukemia and osteoporosis (Dinarello, C. A.; Wolff, S. M., *New Engl. J. Med.,* (1993), 328, 106). A naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., *Nature,* (1990), 343, 336–340; Eisenberg, S. P.; Evans, R. J.; Arend, W. P.; Verderber, E.; Brewer, M. T.; Hannum, C. H.; Thompson, R. C., *Nature* (1990), 343, 341–346; Ohisson, K.; Bjork, P.; Bergenfeldt, M.; Hageman, R.; Thompson, R. C., *Nature,* (1990), 348, 550–552; Wakabayashi, G., *FASEB,* (1991), 338–343; Pacifici, R.; et al. *Proc. Natl. Acad. Sci.* (1989), 86, 2398–2402 and Yamamoto, I.; et al. *Cancer Rsh* (1989), 49, 4242–4246). The specific role of IL-1β in inflammation and immunomodulation is supported by the recent observation that the cowpox virus employs an inhibitor of ICE to suppress the inflammatory response of its host (Ray, C. A. et al, *Cell,* (1992), 69, 597–604).

In summary, the utility of ICE inhibitors in modifying certain IL-1β mediated disease states has been suggested and demonstrated in vivo by several workers in the field (for a leading reference see: Miller, D. K. et al. "The IL-1β Converting Enzyme as a Therapeutic Target" in Immunosuppressive and Antiinflammatory Drugs; Annals of the New York Academy of Sciences; Vol. 696, pp 133–148, 1993). The following review of the current state of the art in ICE research further supports such utility of ICE inhibitors:

1) WO 9309135, published 11 May 1993, teaches that peptide-based aspartic acid arylacyloxy-and aryoxymethyl ketones are potent inhibitors of ICE in vitro. These compounds also specifically inhibited ICE in the whole cell (in vivo) by their ability to inhibit the formation of mature IL-1β in whole cells. These ICE inhibitors also demonstrated utility in reducing fever and inflammation/swelling in rats.

2) Patients with Lyme disease sometimes develop Lyme arthritis. *B. burgdorferi,* the causative agent of Lyme disease, is a potent inducer of IL-1 synthesis by mononuclear cells. Miller et al. (Miller, L. C.; Lynch, E. A. Isa, S.; Logan, J. W.; Dinarello, C. A.; and Steere, A. C., "Balance of synovial fluid IL-1β and IL-1 Receptor Antagonist and Recovery from Lyme arthritis", *Lancet* (1993) 341; 146–148) showed that in patients who recovered quickly from Lyme Arthritis, the balance in synovial fluid of IL-1β and IL-1ra was in favor of IL-ra. When the balance was shifted in favor of IL-1β it took significantly longer for the disease to resolve. The conclusion was that the excess IL-1ra blocked the effects of the IL-1β in the patients studied.

3) IL-1 is present in affected tissues in ulcerative colitis in humans. In animal models of the disease, IL-1β levels correlate with disease severity. In the model, administration of IL-1ra reduced tissue necrosis and the number of inflammatory cells in the colon. See, Cominelli, F.; Nast, C. C.; Clark, B. D.; Schindler, R., Llerena, R.; Eysselein, V. E.; Thompson, R. C.; and Dinarello, C. A.; "Interleukin-1 Gene Expression, Synthesis, and Effect of Specific IL-1 Receptor Blockade in Rabbit Immune Complex Colitis" *J. Clin. Investigations* (1990) Vol. 86, pp, 972–980.

4) IL-1ra supresses joint swelling in the PG-APS model of arthritis in rats. See Schwab, J. H.; Anderle, S. K.; Brown, R. R.; Dalldorf, F. G. and Thompson, R. C., "Pro- and Anti-Inflammatory Roles of Interelukin-1 in Recurrence of Bacterial Cell Wall-induced Arthritis in Rats". *Infect, Immun.* (1991) 59; 4436–4442.

5) IL-1ra shows efficacy in an small open-label human Rheumatoid Arthritis trial. See, Lebsack, M. E.; Paul, C. C.; Bloedow, C. C.; Burch, F. X.; Sack, M. A.; Chase, W., and Catalano, M. A. "Subcutaneous IL-1 Receptor Antagonist in Patients with Rheumatoid Arthritis", *Arth. Rheum.* (1991) 34; 545.

6) Soluble IL-1 receptor significantly reduces clinically the cutaneous late-phase allergic reaction. This was demostrated in a prospective, randomized, double-blind, placebo-controlled study on 15 allergic subjects. See, Mullarkey, M. F. et al. "Human Cutaneous Allergic Late-Phase Response is Inhibited by Soluble IL-1 Receptor", J. of Immunology, (1994) 152; 2033–2041.

7) IL-1 appears to be an autocrine growth factor for the proliferation of chronic myelogenous leukemia cells. Both IL-1ra and sIL-1R inhibit colony growth in cells removed from leukemia patients. See, Estrov, Z.; Kurzrock, R.; Wetzler, M.; Kantarjian, H.; Blake, M.; Harris, D.; Gutterman, J. U.; and Talpaz, M., "Supression of Chronic Myelogenous Leukemia Colony Growth by Interleukin-1 (IL-1) Receptor Antagonist and Soluble IL-1 Receptors: a Novel Application for Inhibitors of IL-1 Activity". *Blood* (1991) 78; 1476–1484.

8) As in 6) above, but for acute myelogenous leukemia rather than chronic myelogenous leukemia. See, Estrov, Z.; Kurzrock, R.; Estey, E.; Wetzler, M.; Ferrajoli, A.; Harris, D.; Blake, M.; Guttermann, J. U.; and Talpaz, M. "Inhibition of Acute Myelogenous Leukemia Blast Proliferation by Interleukin-1 (IL-1) Receptor Antagonist and Soluble IL-1 Receptors". (1992) *Blood* 79; 1938–1945.

The present invention relates to the modulation of processing of IL-1β for the treatment of rheumatoid arthritis.

Levels of IL-1β are known to be elevated in the synovial fluid of patients with the disease. Additionally, IL-1β stimulates the synthesis of enzymes believed to be involved in inflammation, such as collagenase and $PLA_2$, and produces joint destruction which is very similar to rheumatoid arthritis following intra-articular injection in animals.

A limited number of peptidyl methyl ketone analogs constitute a well-known class of compounds having cysteine protease (papain, cathepsin B) inhibition activity. These peptidyl methyl ketone analogs have been reviewed by D. Rich in Chapter 4 of "Protease Inhibitors", Barrett, A. J. and Salvensen, G. eds., Elsevier, 1986. More recently, α-aryloxy and α-arylacyloxy methyl ketones have also been described as inhibitors of cysteine protease (Krantz, A. et al, Biochemistry, 30, p. 4678–4687, 1991).

These peptide analogs, however, are essentially devoid of potency and selectivity in inhibiting ICE.

An effective therapy has yet to be fully developed commercially for the treatment of IL-1β mediated inflammatory diseases. Consequently, there is a need for therapeutic agents effective in the treatment and prevention of these diseases.

SUMMARY OF THE INVENTION

According to the present invention, there is provided a compound of the formula (I) and a pharmaceutically acceptable salt thereof:

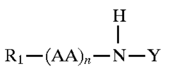

(I)

wherein:

n is 0–4;

Y is

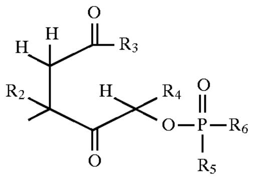

and when $R_3$ is OH, then Y can also be

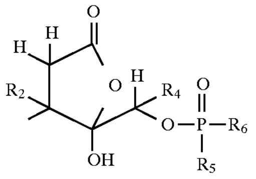

$R_2$ is H or deuterium;

$R_3$ is OH, $OR_7$, $NR_7OR_8$ or $NR_7R_8$;

where $R_7$ and $R_8$ are independently H, alkyl, cycloalkyl, aralkyl, heteroaralkyl, aryl or heteroaryl;

$R_4$ is H or lower alkyl;

$R_5$ and $R_6$ are optionally and independently selected from H, OH, alkyl, aryl, aralkyl, heteroaryl, heteroaralkyl, alkoxy, aroxy, heteroaroxy, aralkoxy, heteroaralkoxy, alkenyl, aralkenyl or heteroaralkenyl;

A preferred embodiment of this invention is where $R_5$ and $R_6$ are aryl.

AA is independently selected from the group consisting of (a) and (b) where (a) is defined as an amino acid of formula II

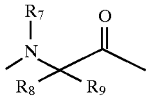

(II)

wherein $R_7$ and $R_8$ are defined as above and $R_9$ is $(CR_6R_7)_{0-6}$—$R_{10}$;

where $R_{10}$ is a radical optionally selected from $R_{11}$, where $R_{11}$ is described below; and where group (b) is selected from the group consisting of:

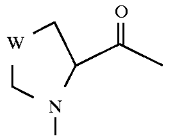

(1)

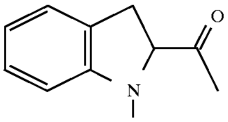

(2)

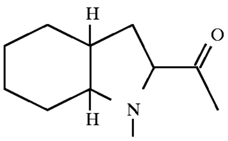

(3)

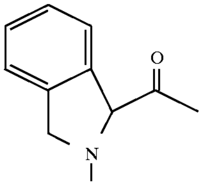

(4)

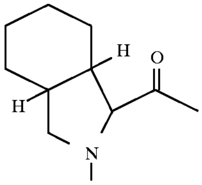

(5)

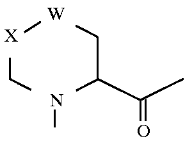

(6)

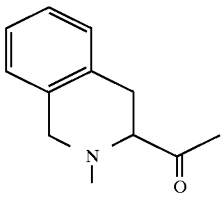

(7)

-continued (8)

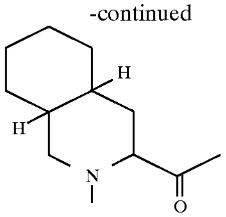

(9)

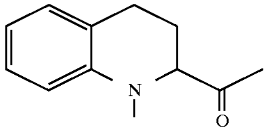

(10)

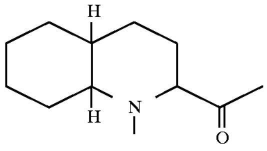

(11)

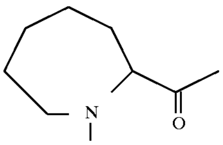

(12)

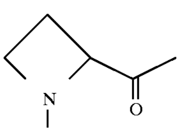

(13)

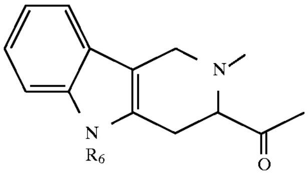

and (14)

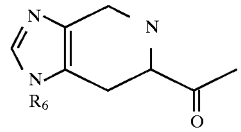

where W and X are optionally $CH_2$, O, S or $NR_7$;

$R_1$ is $R_{10}$—CO— or $R_{10}SO_2$—, where $R_{10}$ is defined previously;

$R_{11}$ is H, alkyl, alkenyl, aryl, heteroaryl, aralkyl, heteroaralkyl, aralkenyl, heteroaralkenyl, hydroxy, alkoxy, 2-(alkyoxy)ethoxy, 2-(alkyoxy)aminoethyl and 2-(alkyoxy)-N-alkylaminoethyl, aralkoxy, heteroaralkoxy, alkylacyloxy, aralkylacyloxy, heteroaralkylacyloxy, aracyloxy, heteroaracyloxy, aryloxyalkylacyloxy, heteroaryloxyalkylacyloxy, alkylacyl, aralkylacyl, heteroaralkylacyl, alkylacylamino, aralkylacylamino, heteroaralkylacylamino, aracylamino, heteroaracylamino, aryloxyalkylacylamino, heteroaryloxyalkylacylamino, alkyloxyalkylacylamino, alkoxyacylamino, aralkoxyacylamino, heteroaralkoxyacylamino, aracyl, heteroaracyl, aryloxyalkylacyl, heteroaryloxyalkylacyl, halo, haloalkyl, guanidino, mono- and di-alkylguanidino, mono- and di-aralkylguanidino, mono- and di-heteroaralkylguanidino, alkylacylguanidino, aralkylacylguanidino, heteroaralkylguanidino, aracylguanidino, heteroarylguanidino, amidino, mono- and di-alkylamidino, mono- and diaralkylamidino, mono- and di-heteroaralkylamidino, amino, mono- and dialkylamino, mono- and di-aralkylamino, mono- and di-heteroaralkylamino, carboxy, alkylcarboxy, carbalkoxy, carbalalkoxy, carbheteroaralkoxy, carbalkoxyalkenyl, carboxamido, mono- and dialkylcarboxamido, mono- and diarcarboxamido, mono and di-heteroarcarboxamido, mono- and di-aralkylcarboxamido, mono- and di-heteroaralkylcarboxamido, thio, alkylthio, arylthio, heteroarylthio, aralkylthio, heteroaralkylthio, sulfonamido, mono- and di-alkylsulfonamido, mono- and di-aralkylsulfonamido, mono- and di-heteroaralkylsulfonamido, morpholinosulfonamido, alkylsulfonyl, aralkylsulfonyl, heteroaralkylsulfonyl, arylsulfonyl, heteroarylsulfonyl, nitro, cyano, N-morpholinoalkyl, N-morpholinoalkoxy, N-morpholinoaralkyl, N-morpholinoaralkoxy, N-morpholinoheteroaralkyl, N-morpholinoheteroaralkoxy, N-mono and N,N-dialkylaminoalkyl and N-mono- and N,N-dialkylaminoethoxy, quinuclidinylamino, quinuclidinyloxy, quinuclidinocarbonyl or ureido.

Heteroaryl is defined as an unsubstituted or an optionally substituted mono- or bicyclic ring system of about 5 to about 12 carbon atoms and where each monocyclic ring may possess from 0 to about 4 heteroatoms, and each bicyclic ring may possess about 0 to about 5 heteroatoms selected form N, O, and S provided said heteroatoms are not vicinal oxygen and/or sulfur atoms and were the substituents, numbering from 0 to about 5 may be located at any appropriate position of the ring system and are described by $R_{11}$.

Examples of such mono- and bicyclic ring systems which are by no means meant to limit the scope of this invention, include benzofuran, benzothiophene, indole, benzopyrazole, coumarin, isoquinoline, pyrrole, thiophene, furan, thiazole, imidazole, pyrazole, triazole, quinoline, pyrollidenone, pyrimidine, pyridine, pyridone, pyrazine, pyridazine, isothiazole, isoxazole and tetrazole.

The pharmaceutically acceptable salts include both acid and base addition salts.

The term acid addition salts refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases which include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like.

Particularly preferred organic non-toxic bases are isopropylamine, diethylamine, ethanolamine, trimethamine, dicyclohexylamine, choline and caffeine.

As employed above and throughout the disclosure, the following terms, unless otherwise indicated, shall be understood to have the following meanings:

"Alkyl" is defined as a saturated aliphatic hydrocarbon which may be either straight- or branched-chain or cyclic. Preferred groups have no more than about 12 carbon atoms and may be methyl, ethyl and structural isomers of propyl, butyl, pentyl, hexyl, heptyl, octyl, nonyl, decyl, undecyl, dodecyl, cyclopropyl, cyclobutyl, cyclopentyl, cyclohexyl, cycloheptyl and cyclooctyl.

"Aryl" is defined as a phenyl or naphthyl or a substituted phenyl and a substituted naphthyl ring wherein one or more of the hydrogens has been replaced by the same or different substituents as selected from $R_{11}$.

"Alkoxy" refers to an alkyl-O-group. For example, methoxy or ethoxy.

"Aryloxy" refers to an aryl-O-group. For example, phenoxy.

"Heteroxy" refers to a hetero-O-group. For example, 4-pyridyloxy.

"Aralkyl" refers to an alkyl group substituted by an aryl radical. For example, benzyl.

"Heteroaralkyl" refers to an alkyl group substituted by a heteroaryl radical. For example, (4-pyridyl)methyl.

"Alkenyl" is defined as an unsaturated aliphatic hydrocarbon which may be either straight- or branched-chain or cyclic. Preferred groups have no more than about 12 carbon atoms and no fewer than 2 carbon atoms and contain from one to up to about 6 double bonds. Examples of alkenyl groups include ethenyl, propenyl, 1-hexenyl, 1-3-hexdienyl, 2-methyl-2-butenyl, 2-methyl-3-pentenyl, cyclopentenyl, cyclohexenyl and cyclobutenyl.

"Alkylacyl" refers to an alkyl-C(O)-group. For example, acetyl or propionyl.

"Alkylacyloxy" refers to an alkyl-C(O)O-group. For example, an acetoxy group.

"Alkylacylamino" means alkyl-C(O)—$NR_7$ where $R_7$ has been defined previously.

"Alkylacylguanidino" means alkyl-C(O)$NR_6$C($NR_7$)NH— where $R_6$ and $R_7$ have been defined previously.

"Ureido" refers to an $R_6R_7$N—C(O)—N—$R_6$-group where $R_6$ and $R_7$ are described previously.

"Haloalkyl" is defined as a saturated aliphatic hydrocarbon of 1–12 carbon atoms which may be either straight- or branched-chain or cyclic and where one or more of the hydrogen atoms is replaced with halogen. Preferred haloalkyl groups include trifluoromethyl and pentafluoroethyl.

"Halo" means bromo, chloro and fluoro.

The present invention concerns a method for inhibiting ICE in a mammal by administering a therapeutically effective amount of a compound of the Formula (I) or a pharmaceutical composition containing a compound of the Formula (I) in a pharmaceutically acceptable carrier. The method of inhibition is directed for the treatment of IL-1β mediated disease states or disorders which include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseass, such as hypersensitivity; auto-immune diseases, such as multiple sclerosis; bone diseases; and certain tumors.

The pharmaceutical composition of the present invention comprises an active ingredient of the compound of the formula (I) in admixture with a pharmaceutically acceptable, non-toxic carrier. Such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet , capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, syrup, methylcellulose, polyoxyethylene sorbitan monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences,* 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition of acylcarnitines (*Am. J. Physiol.* 251:3332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt. 2, B. H. Vickery and J. S. Nester, Eds., MTP Press, Lancaster, UK, 1987).

In general, for the uses as described in the instant invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 to mg/kg to about 10 mg/kg of body weight.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

DETAILED DESCRIPTION OF THE INVENTION

The compounds of this invention are prepared by one of two related general synthetic methods as described in Schemes 1 and 2. Referring to Scheme I, the first step of the method involves the synthesis of Z-protected amino acid bromomethyl ketones (formula 2), where the "Z-group" refers to the "benzyloxycarbonyl group". Methods for the preparation of various Z-protected aspartic acids and aspartic acid-containing peptides (formula 1) which are used as the starting materials for the synthesis of the bromomethyl ketones (formula 2), are well established in the art. ("The Peptides" E. Gross and J. Meienhofer, Eds. Academic Press, Orlando, Fla.; 1979; Vol. 1–3.) The Z-protected amino acids, dipeptides, and polypeptides (formula 2), which in some cases are commercially available, are then converted to the aspartic acid-containing bromomethylketones (formula 2), by way of hydrobromination of a diazomethyl ketone intermediate. This is accomplished by methods described in Shaw, E. and Ruscica, J., *J. Biol. Chem.,* 1968, 243, 6312 and Green, E. D. J. and Shaw, E., *J. Biol. Chem.,* 1981, 256, 1923.

The t-butyl ester bromoketone (formula 2) is reacted with a variety of phosphinic acids. This is conducted by exposing the bromomethyl ketone to an excess of the phosphinic acids in a DMF containing sodium or potassium hydride or potassium fluoride. The reaction can be conveniently monitored by thin layer chromatography (TLC) and once the TLC indicates that the displacement of the bromide with the phosphinic acids is completed, the product is isolated using standard procedures. The desired aspartic acid-based mono-t-butyl ester phosphinyloxymethyl ketones (formula 3) may be purified by conventional methods including recrystallization and silica gel column chromatography.

SCHEME 1

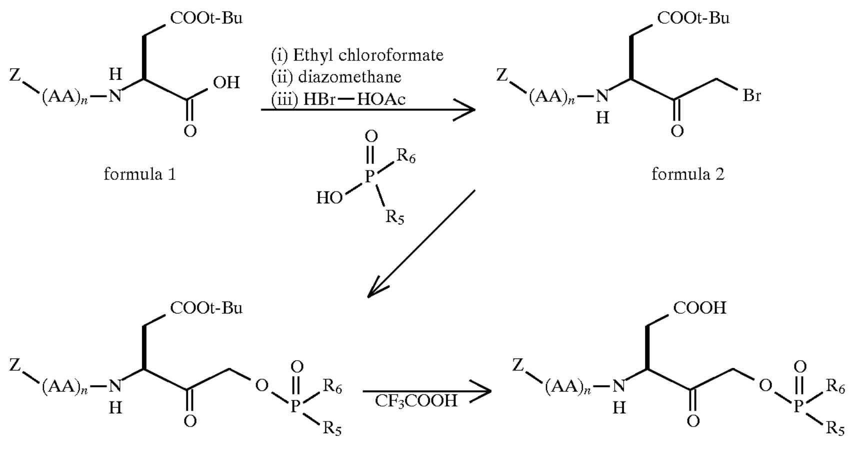

formula 1
formula 2
formula 3
formula 4

SCHEME 2

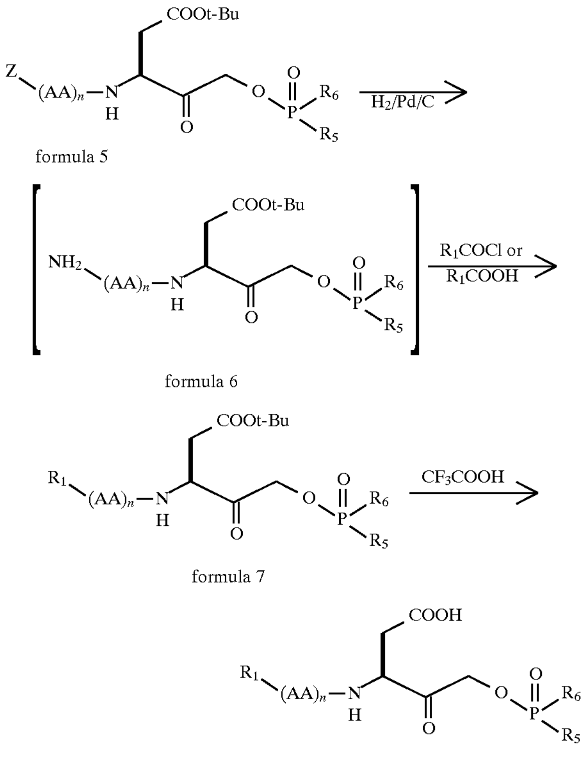

formula 5
formula 6
formula 7
formula 8 wherein

AA, $R_1$, $R_5$, and $R_6$ are as defined in formula (I) and Z is defined as the benzyloxycarbonyl group.

The remaining synthetic transformation to generate the ICE inhibitors is hydrolysis of the t-butyl ester function. This is conducted by exposing the ester to a 25% solution of trifluoroacetic acid at 25° C. The de-esterification is usually complete within 3 h and the removal of the volatile TFA and solvent affords the aspartic acid derivative in formula 4. The yield of the reaction is quantitative in most instances, providing the t-butyl ester starting material is of high purity. Purification, if required, can be performed by recrystallization or chromatographic techniques which are well known to those skilled in the art. A solution of 3 molar anhydrous HCl in ethyl acetate may be used in place of TFA-methylene chloride solution with equal efficiency.

In Scheme 2, the synthesis of phosphinyloxymethyl ketones which possess an N-terminal group (other than the Z group) are described. The aspartic acid derivatives of formula 5 are the starting material for the synthesis of these compounds. The Z group is removed to generate an N-terminal amine (formula 6) under hydrogenolytic conditions. The reagents and conditions used to carry out the hydrogeneration reaction are hydrogen gas, ambient temperature and pressure, 5%-Pd/C as the catalyst in an alcoholic solvent (ethanol), optionally containing 2 equivalents of hydrochloric acid.

The N-terminal amine is then condenced with a carboxylic acid chloride or an active carboxylic acid ("The Practice of Peptide Synthesis", M Bodanszky, Springer-Verlag, N.Y., 1984) to yield an amide (formula 7). Lastly, the t-butyl ester is removed with trifluoroacetic acid to afford the aspartic acid derivative (formula 8).

The phosphinic acids used in the reaction with the bromomethyl ketones can be either purchased from commercial sources or synthesized by adopting known procedures. Their synthesis is readily deduced by those skilled in the art of organic synthesis.

The following examples will further illustrate the compounds of the present invention.

EXAMPLE 1

N-[4-(N,N-Dimethylaminomethyl)]benzoyl-L-valyl-L-aspartic acid diphenylphosphinyloxymethyl ketone Part A: N-Benzyloxycarbonyl-L-valine-L-aspartic acid bromomethyl ketone β-tert butyl ester (1.16 mmol; Formula 2) was dissolved in 2 mL of DMF containing diphenylphosphinic acid (1.4 mmol) and powdered anhydrous KF (1.6 mmol). The reaction mixture was stirred under $N_2$ for 16 hrs. The mixture was diluted with water (30 mL), extracted with ether (3×20 mL), and the organic layer was washed with 0.1 N NaOH (3×10 mL) followed by brine. The ether solution was dried over magnesium sulfate and concentrated in vacuo to afford (80%) of the β-tert-butyl ester (formula 3) as a tan solid.

Part B: N-Benzyloxycarbonyl-L-valine-L-aspartic acid diphosphinyloxymethyl ketone β-tert-butyl ester (2 mmol; Part A above) was dissolved in absolute ethanol (100 mL) containing 2 equiv. of 6 N aqueous HCI (4 mmol) and a catalytic amount of 10% palladium on carbon. The reaction mixture was stirred under an ambient atmosphere of $H_2$ gas for about 1 hr. The solution was filtered and the solvent was removed in vacuo to give the corresponding HCl-salt (formula 6) which was used immediately in the subsequent reaction.

Part C: The HCl-salt obtained in Part B above was dissolved in $CH_2Cl_2$ (10 mL), cooled to −20° C. and N-[4-(N,N-dimethylaminomethyl)]benzoyl chloride (4 mmol) was added followed by the addition of 10 mg of dimethylamino pyridine (DMAP) and N-methylmorpholine (5 mmol). The reaction mixture was stirred for 2 hrs at 25° C. The solvent was removed in vacuo and the residue was dissolved in EtOAc (10 mL) which was then washed with water, 0.01 N aqueous HCl, saturated $NaHCO_3$, brine and dried over $MgSO_4$. The EtOAC was removed in vacuo and the residue was purified by silica gel chromatography ($CH_2Cl_2$-MeOH) to obtain N-(4-(N,N-dimethylaminomethyl)benzoyl-L-vali ne-L-aspartic acid diphenylphosphinyloxymethyl ketone β-tert-butyl ester (formula 7) in 50% yield.

Part D: The β-tert-butyl ester obtained in Part C above (1 mmol) was dissolved in trifluoroacetic acid—$CH_2Cl_2$ (1:4) and the solution was stirred for 2 hrs at 25° C. The solvent was removed in vacuo and the residue was triturated with ether. The white solid was collected and dried to give the title compound in 90% yield. Mass spectrum: m/z 608 (M+H).

The 4-(N,N-dimethylaminomethyl) benzoyl chloride was prepared by reacting the acid with excess oxalyl chloride for 1 hr at 25° C. The 4-(N,N-dimethylaminomethyl) benzoic acid was in turn prepared from methyl 4-aminomethylbenzoate via reductive alkylation ($CH_2O$, $Na(OAc)_3BH$ as in *J. Org. Chem.,* 1972, 37, 1673) followed by hydrolysis using 10% aqueous NaOH.

Following the procedure described in Schemes 1 and 2 and by analogy to Example 1, the following compounds were prepared.

EXAMPLE 2

N-Benzyloxycarbonyl-L-valyl-L-aspartic acid diphenylphosphinyloxymethyl ketone Mass spectrum: m/z=581 [M+H]

EXAMPLE 3

N-Benzyloxycarbonyl-L-aspartic acid diphenylphosphinyloxymethyl ketone. Mass spectrum: m/z=596 [M+H]

EXAMPLE 4

N-Benzyloxycarbonyl-L-aspartic acid (p-chlorophenyl)-phenyl-phosphinyloxymethyl ketone. Mass spectrum: m/z=516 [M+H]

EXAMPLE 5

N-Benzyloxycarbonyl-L-aspartic acid (p-methoxyphenyl)-phenyl-phosphinyl-oxymethyl ketone. Anal. Calcd. for $C_{31}H_{35}N_2O_9P{\cdot}0.5\ CF_3CO_2H{\cdot}0.5H_2O$: C,56.80; H, 5.44; N, 4.14. Found: C, 56.85; H, 5.33; N, 4.15.

EXAMPLE 6

N-Benzyloxycarbonyl-L-valyl-L-alanyl-L-aspartic acid diphenylphosphinyloxy-methylketone. Mass spectrum: m/z=652 [M+H]

EXAMPLE 7

N-[4-(N,N-Dimethylaminomethyl)]benzoyl-L-valyl-L-alanyl-L-aspartic acid diphenylphosphinyloxymethylketone. Mass spectrum: m/z=679 [M+H]

EXAMPLE 8

N-Benzyloxycarbonyl-L-valyl-L-aspartic acid (p-methoxyphenyl)-phenyl-phosphinyloxymethyl ketone. Mass spectrum: m/z=611 [M+H]

EXAMPLE 9

N-Benzyloxycarbonyl-L-valyl-L-aspartic acid (p-chlorophenyl)-phenyl-phosphinyloxymethyl ketone. Mass spectrum: m/z=616 [M+H]

EXAMPLE 10

N-Benzyloxycarbonyl-L-aspartic acid di-(p-methoxyphenyl)phosphinyloxy-methyl ketone. Anal. Calcd. for $C_{27}H_{28}NO_9P{\cdot}0.5\ CF_3CO_2H$: C, 56.19; H, 4.80; N, 2.34. Found: C, 55.98, H, 4.77; N, 2.38.

EXAMPLE 11

N-Benzyloxycarbonyl-L-aspartic acid (m-methoxyphenyl)-phenyl-phosphinyloxymethyl ketone. Anal. Calcd. for $C_{26}H_{26}NO_8P{\cdot}0.5\ CF_3CO_2H$: C, 57.05; H, 4.70; N, 2.46. Found: C, 57.29; H, 4.78; N, 2.50.

EXAMPLE 12

N-4-(Pyridyl)carbomethoxy-L-valyl-L-alanyl-L-aspartic acid diphenylphosphinyl-oxymethyl ketone. Mass spectrum: m/z=767 [M+H]

EXAMPLE 13

N-Benzyloxycarbonyl-L-valyl-D-aspartic acid diphenylphosphinyloxymethyl ketone Mass spectrum: m/z=581 [M+H]

EXAMPLE 14

N-3-(Quinuclidinyl)carbonyl-L-valyl-L-alanyl-L-aspartic acid diphenyl-phosphinyloxymethyl ketone. Mass spectrum: m/z=769 [M+H]

EXAMPLE 15

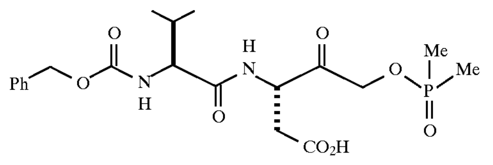

N-Benzyloxycarbonyl-L-valyl-L-aspartic acid dimethylphosphinyloxymethyl ketone Mass Spectrum m/z=457 (M+H)

EXAMPLE 16

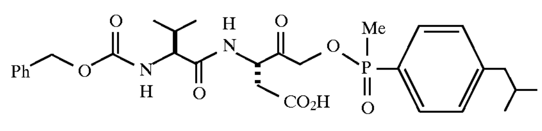

N-Benzyloxycarbonyl-L-valyl-L-aspartic acid (methyl) (4-(2-methylpropyl)phenyl)-phosphinyloxymethyl ketone Mass Spectrum m/z=589 (M+H)

EXAMPLE 17

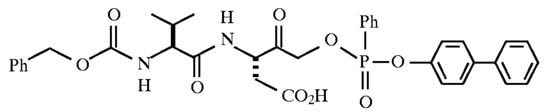

N-Benzyloxycarbonyl-L-valyl-L-aspartic acid (phenyl)((4-phenyl)phenyl)phosphinyl-oxymethyl ketone Mass Spectrum m/z=678 (M+H)

EXAMPLE 18

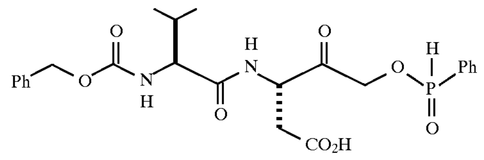

N-Benzyloxycarbonyl-L-valyl-L-aspartic acid phenylphosphinyloxymethyl ketone Mass Spectrum m/z=589 (M+H)

EXAMPLE 19

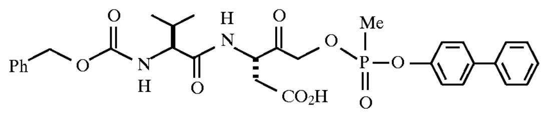

N-Benzyloxycarbonyl-L-valyl-L-aspartic acid (methyl)((4-phenyl)phenyl)phosphinyl-oxymethyl ketone Mass Spectrum m/z=609 (M+H)

Compounds of the present invention were tested for IL-1β protease inhibition activity according to the following protocol:

Partially purified IL-1β protease is stored at −80° C., thawed on ice, and preincubated for 10 minutes at 37° C. with 2.5 mM dithiothreitol in a buffer solution containing 10 mM Tris-HCl (pH 8.0) and 25% (v/w) glycerol. Inhibitors are prepared as stock solutions in dimethyl sulfoxide (DMSO). The protease is preincubated with inhibitor in a volume of 20 $\mu$L in a 1.5 mL polypropylene microcentrifuge tube for 15 minutes at 37° C. The volume of compound added to the assay is adjusted to yield a DMSO concentration in the preincubation of <15% (v/v). The enzyme assay is then initiated by the addition of substrate (TRITC-AYVHDAPVRS-$NH_2$) SEQ ID No. 1 to yield a final concentration of 67 $\mu$M in a final volume of 30 $\mu$L. The reaction are carried out for 60 minutes at 37° C. in the dark and are terminated by the addition of 10 $\mu$L of 10% trifluoroacetic acid (TFA). Following the addition of 115 $\mu$L of 0.1% TFA, the samples are analyzed by high pressure liquid chromatography using a reverse phase (C18) column and elution with an acetonitrile/water/TFA gradient. Substrate and product are monitored by their absorbance at 550 nm and elute at 4.2 and 5.2 minutes, respectively.

The IC50 values recorded for inhibition against the enzyme were <10 $\mu$m.

The invention, having been fully described, it will be apparent to one skilled in the art that changes and modifications can be made thereto without departing from the spirit and scope thereof.

What is claimed is:

1. A compound of the formula (I) or a pharmaceutically acceptable salt thereof:

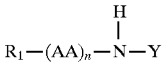

(I)

wherein:

n is 0–4;

Y is

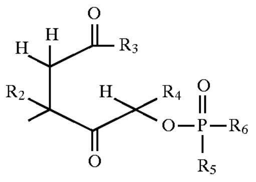

and when $R_3$ is OH, then Y can also be

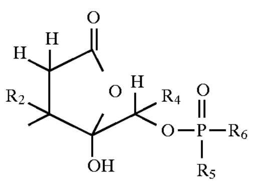

$R_2$ is H or deuterium;

$R_3$ is OH, $OR_7$, $NR_7OR_8$ or $NR_7R_8$;

where $R_7$ and $R_8$ are independently H, alkyl, cycloalkyl, benzyl, or phenyl;

$R_4$ is H or lower alkyl;

$R_5$ and $R_6$ are optionally and independently selected from H, OH, alkyl, alkoxy, and phenyloxy;

AA is independently selected from the group consisting of (a) and (b) where (a) is defined as an amino acid of formula II

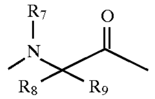

(II)

wherein $R_7$ and $R_8$ are defined as above and $R_9$ is $(CR_6R_7)_{0-6}$—$R_{10}$;

where $R_{10}$ is a radical optionally selected from $R_{11}$, where $R_{11}$ is described below; and where group (b) is selected from the group consisting of:

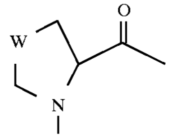

(1)

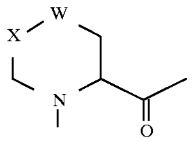

(6)

where W and X are optionally $CH_2$, or O;

$R_1$ is $R_{10}$—CO—, where $R_{10}$ is defined previously;

$R_{11}$ is H, alkyl, alkenyl, hydroxy, benzyl, alkoxy, 2-(alkyoxy)ethoxy, 2-(alkyoxy)aminoethyl and 2-(alkyoxy)-N-alkylaminoethyl, alkylacyloxy, alkylacyl, halo, haloalkyl, guanidino, mono- and di-alkylguanidino, alkylacylguanidino, alkylacylguanidino, amidino, mono- and di-alkylamidino, amino, mono- and dialkylamino, carboxy, alkylcarboxy, carbalkoxy, carbalalkoxy, carbalkoxyalkenyl, carboxamido, mono- and dialkylcarboxamido, mono- and diarcarboxamido, thio, alkylthio, sulfonamido, mono- and di-alkylsulfonamido, morpholinosulfonamido, alkylsulfonyl, nitro, cyano, N-morpholinoalkyl, N-morpholinoalkoxy, N-mono and N,N-dialkylaminoalkyl and N-mono- and N,N-dialkylaminoethoxy.

2. The compound according to claim 1 selected from the group consisting of: N-[4-(N,N-Dimethylaminomethyl)] benzoyl-L-valyl-L-aspartic acid diphenylphosphinyloxymethyl ketone, N-Benzyloxycarbonyl-L-valyl-L-aspartic acid diphenylphosphinyloxymethyl ketone, N-Benzyloxycarbonyl-L-aspartic acid diphenylphosphinyloxymethyl ketone, N-Benzyloxycarbonyl-L-aspartic acid (p-chlorophenyl)-phenyl-phosphinyloxymethyl ketone and N-Benzyloxycarbonyl-L-aspartic acid (p-methoxyphenyl)-phenyl-phosphinyl-oxymethyl ketone.

3. The compound according to claim 1 selected from the group consisting of: N-Benzyloxycarbonyl-L-valyl-L-alanyl-L-aspartic acid diphenylphosphinyloxymethylketone, N-[4-(N,N-Dimethylaminomethyl)]benzoyl-L-valyl-L-alanyl-L-aspartic acid diphenylphosphinyloxymethylketone, N-Benzyloxycarbonyl-L-valyl-L-aspartic acid (p-methoxyphenyl)-phenyl-phosphinylmethyl ketone, N-Benzyloxycarbonyl-L-valyl-L-aspartic acid (p-chlorophenyl)-phenyl-phosphinyloxymethyl ketone and N-Benzyloxycarbonyl-L-aspartic acid di-(p-methoxyphenyl)phosphinyloxymethyl ketone.

4. The compound according to claim 1 selected from the group consisting of: N-Benzyloxycarbonyl-L-aspartic acid (m-methoxyphenyl)-phenyl-phosphinyloxymethyl ketone, N-4-(Pyridyl)carbomethoxy-L-valyl-L-alanyl-L-aspartic acid diphenylphosphinyl-oxymethyl ketone, N-Benzyloxycarbonyl-L-valyl-D-aspartic acid diphenylphosphinyloxymethyl ketone and N-3-(Quinuclidinyl) carbonyl-L-valyl-L-alanyl-L-aspartic acid diphenylphosphinyloxymethyl ketone.

5. A pharmaceutical composition for inhibiting interleukin-1β protease comprising a compound of the formula (I) or a pharmaceutically acceptable salt thereof:

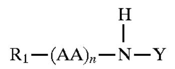
(I)

wherein:

n is 0–4;

Y is

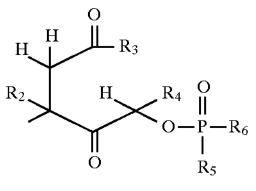

and when $R_3$ is OH, then Y can also be

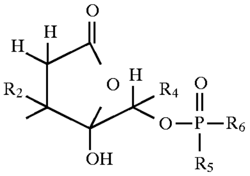

$R_2$ is H or deuterium;

$R_3$ is OH, $OR_7$, $NR_7OR_8$ or $NR_7R_8$;

where $R_7$ and $R_8$ are independently H, alkyl, cycloalkyl, benzyl, or phenyl;

$R_4$ is H or lower alkyl;

$R_5$ and $R_6$ are optionally and independently selected from H, OH, alkyl, alkoxy, and phenyloxy;

AA is independently selected from the group consisting of (a) and (b) where (a) is defined as an amino acid of formula II

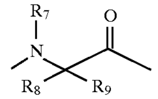
(II)

wherein $R_7$ and $R_8$ are defined as above and $R_9$ is $(CR_6R_7)_{0-6}$-$R_{10}$;

where $R_{10}$ is a radical optionally selected from $R_{11}$, where $R_{11}$ is described below; and where group (b) is selected from the group consisting of:

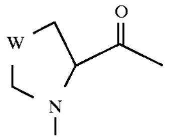
(1)

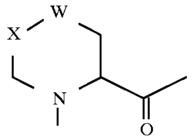
(6)

where W and X are optionally $CH_2$, or O;

$R_{11}$ is $R_{10}$—C—, where $R_{10}$ is defined previously;

$R_{11}$ is H, alkyl, alkenyl, hydroxy, benzyl, alkoxy, 2-(alkyoxy)ethoxy, 2-(alkyoxy)aminoethyl and 2-(alkyoxy)-N-alkylaminoethyl, alkylacyloxy, alkylacyl, halo, haloalkyl, guanidino, mono- and di-alkylguanidino, alkylacylguanidino, amidino, mono- and di-alkylamidino, amino, mono- and dialkylamino, carboxy, alkylcarboxy, carbalkoxy, carbalalkoxy, carbalkoxyalkenyl, carboxamido, mono- and dialkylcarboxamido, mono- and diarcarboxamido, thio, alkylthio, sulfonamido, mono- and di-alkylsulfonamido, morpholinosulfonamido, alkylsulfonyl, nitro, cyano, N-morpholinoalkyl, N-morpholinoalkoxy, N-mono and N,N-dialkylaminoalkyl and N-mono- and N,N-dialkylaminoethoxy, in combination with a pharmaceutically acceptable carrier.

6. The pharmaceutical composition of claim 5 wherein said compound is selected from the group consisting of: N-[4-(N,N-Dimethylaminomethyl)] benzoyl-L-valyl-L- aspartic acid diphenylphosphinyloxymethyl ketone, N-Benzyloxycarbonyl-L-valyl-L-aspartic acid diphenylphosphinyloxymethyl ketone, N-Benzyloxycarbonyl-L-aspartic acid diphenylphosphinyloxymethyl ketone, N-Benzyloxycarbonyl-L-aspartic acid (p-chlorophenyl)-phenyl-phosphinyloxymethyl ketone and N-Benzyloxycarbonyl-L-aspartic acid (p-methoxyphenyl)-phenyl-phosphinyl-oxymethyl ketone.

7. The pharmaceutical composition of claim 5 wherein said compound is selected from the group consisting of: N-Benzyloxycarbonyl-L-valyl-L-alanyl-L-aspartic acid diphenyl-phosphinyloxymethylketone, N-[4-(N,N-Dimethylaminomethyl)]benzoyl-L-valyl-L-alanyl-L-aspartic acid diphenylphosphinyloxymethylketone, N-Benzyloxycarbonyl-L-valyl-L-aspartic acid (p-methoxyphenyl)-phenyl-phosphinyloxymethyl ketone, N-Benzyloxycarbonyl-L-valyl-L-aspartic acid (p-chlorophenyl)-phenyl-phosphinyloxymethyl ketone and N-Benzyloxycarbonyl-L-aspartic acid di-(p-methoxyphenyl)phosphinyloxymethyl ketone.

8. The pharmaceutical composition of claim 5 wherein said compound is selected from the group consisting of: N-Benzyloxycarbonyl-L-aspartic acid (m-methoxyphenyl)-phenyl-phosphinyloxymethyl ketone, N-4-(Pyridyl) carbomethoxy-L-valyl-L-alanyl-L-aspartic acid diphenylphosphinyl-oxymethyl ketone, N-Benzyloxycarbonyl-L-valyl-D-aspartic acid diphenylphosphinyloxymethyl ketone and N-3-(Quinuclidinyl) carbonyl-L-valyl-L-alanyl-L-aspartic acid diphenylphosphinyloxymethyl ketone.

* * * * *